United States Patent [19]

Moran et al.

[11] 4,242,186
[45] Dec. 30, 1980

[54] LOW PRESSURE TRITIATION OF MOLECULES

[75] Inventors: Thomas F. Moran; James C. Powers; Mark O. Lively, III, all of Atlanta, Ga.

[73] Assignee: Georgia Tech Research Institute, Atlanta, Ga.

[21] Appl. No.: 24,192

[22] Filed: Mar. 27, 1979

[51] Int. Cl.² .............................................. B01J 1/10
[52] U.S. Cl. .................... 204/157.1 H; 204/158 HE; 204/159.11; 204/160.1; 423/644; 424/1; 23/230.6
[58] Field of Search ................. 204/157.1 H, 158 HE, 204/158 N, 158 ST, 159.11, 160.1; 423/644; 426/313; 23/230.6; 424/1; 252/301.1 R

[56] References Cited

U.S. PATENT DOCUMENTS

| | | | |
|---|---|---|---|
| 3,238,139 | 3/1966 | Fischer et al. | 204/158 HE |
| 4,162,142 | 7/1979 | Ehrenkaufr et al. | 424/1 |

*Primary Examiner*—Howard S. Williams
*Attorney, Agent, or Firm*—Newton, Hopkins & Ormsby

[57] ABSTRACT

Molecules are tritiated by depositing molecules of a substance to be tritiated on a supporting substrate in a vacuum chamber, and then subjecting the substance to low pressures of tritium gas. In a second embodiment of the invention, a substance is tritiated by placing the same near, but not in the path of, an electron beam which traverses a chamber; admitting tritium gas into the chamber; and subjecting the tritium to the electron beam thereby generating vibrationally excited tritium gas molecules which collide and react with the substance thus incorporating tritium atoms into the substance.

47 Claims, 4 Drawing Figures

LOW PRESSURE TRITIATION OF MOLECULES

BACKGROUND OF THE INVENTION

1. Field of the Invention

The present invention relates to a method of introducing tritium into various compounds. More particularly, the present invention relates to a method of introducing tritium into sensitive biological molecules such as proteins, peptides, nucleic acids, polysaccharides, amino acids, polymers, inorganic compounds as well as simple organic molecules.

2. Description of the Prior Art

Tritium labeled compounds are widely used in medicine and in the study of biological problems. The advantage of using tritium as a label resides in the low cost of the isotope and the high specific radioactivity that can be achieved in the labeled material. Because of the ubiquitous nature of hydrogen in organic compounds, almost any compound of medical or biological interest can potentially be labeled with tritium. Substitution of tritium atoms for hydrogen usually results in no significant alteration in the chemical or biological properties of the compound labeled.

The incorporation of tritium into organic molecules including proteins can be achieved by synthetic, biosynthetic and non-synthetic methods. Non-synthetic methods include: (1) self-irradiation of a substance with tritium (Wilzbach labeling), (2) excitation and ionization of a substance induced by microwaves, an electrical discharge, γ-ray irradiation, or the like (modifications of the Wilzbach procedure), (3) recoil tritiums from nuclear reactions, (4) free radical interceptor methods, and (5) exchange reactions catalyzed by acid, bases or other catalysts. Most of these methods have been developed for use with simple organic compounds. However, very few of the methods have been applied to the labeling of complex biological molecules such as proteins, nucleic acids, lipids or polysaccharides. In addition simpler organic molecules which are difficult to isolate or synthesize can only rarely be obtained in a tritiated form using these methods.

Most tritium labeled proteins, nucleic acids, lipids and polysaccharides are produced by biosynthetic methods or by chemical modification. Tritium can be incorporated into biological molecules by these methods often with very high specific activities. However, these methods do not find general utility and are limited to particular systems. The development of a biosynthetic method for the production of a labeled protein is usually more difficult than the isolation of the protein itself and is quite time consuming. In fact, human proteins are difficult or impossible to obtain labeled by biosynthetic methods. Chemical methods for incorporation of labels into such proteins often yield impure products or result in alteration or loss of biological activity.

Non-synthetic methods of tritium labeling have been applied to proteins, but with only limited success. This is evident from the fact that there is only a small number of recent literature citations in the major scientific journals describing non-synthetic tritium labeling methods. In addition, an examination of catalogs of major suppliers of radiochemicals reveals that almost no tritium labeled proteins are commercially available. In fact, the only proteins that are available in any significant number are those which have been labeled with iodine-125. The available nucleic acids, lipids and polysaccharides have usually been produced biosynthetically by bacteria.

Wilzbach (J. Am. Chem. Soc. 78, 5132 (1956) and 79, 1013 (1957)) originally reported that organic compounds can incorporate tritium if exposed to large amounts of tritium gas for long periods of time. In general, the incorporation of tritium into sugars, steroids and aromatic hydrocarbons is relatively good, whereas in the case of polypeptides and aliphatic hydrocarbons, the tritium incorporation is relatively poor. The labeling technique of Wilzbach results in considerable destruction of the sample and in the case of amino acids, it has been shown to result in partial recemization and reduction of the aromatic ring of phenylalinine (Parmentier, J. Label, Compd. 1, 93 (1965) and 2, 367 (1966)).

The proteins lysozyme and ribonuclease have been labeled by the Wilzbach procedure (Steinberg et al., Science 126, 448 (1957)). With lysozyme, only half of the nonexchangeable tritium was found in the active enzyme peak upon chromatography, showing that extensive decomposition had occurred in the labeling reaction. Likewise, ribonuclease was obtained with 82% enzyme activity and again was separated from a degraded fraction of high specific radioactivity.

The peptide hormones insulin and oxytocin have both been labeled by the Wilzbach procedure. With insulin, repeated crystallization or electrophoresis and crystallization was necessary to purify the protein (Von Holt et al., Biochem, biophys. Acta 38, 88 (1960)). Oxytocin labeled by the Wilzbach method had a specific activity of 12 $\mu$Ci/mg (Du Vigneaud et al., J. Am. Chem. Soc. 84, 409 (1962)). After electrophoresis only a small fraction of the radioactivity was bound by the hormone. All of the component amino acids were labeled. The biological potency of the purified oxytocin was only 60% of nonlabeled oxytocin.

There have been many other attempts to apply the Wilzbach procedure to proteins, and it appears that the successful attempts have been substantially outnumbered by failures. In many cases the protein is inactive after labeling (gonadotropin, γ-globulin, or tetanus toxin) and in these cases no purification was attempted or no biological activities were measured. Thus, it seems that the Wilzbach procedure results in gross destruction of the protein with the generation of multiple impurities. The few proteins which were carefully purified showed low specific activities. Thus, this method has very limited usefulness.

A number of procedures have been developed which are modifications of the procedure by Wilzbach. These procedures involve exposure of the compound to tritium gas followed by activation of the tritium with either an electrical discharge or by a microwave generator.

Fisher et al, U.S. Pat. No. 3,238,139, discloses a process for incorporating tritium into organic compounds by subjecting organic compounds to an electric discharge in the presence of tritium gas. Fisher et al suggests that tritium incorporation occurs primarily through reaction of organic radicals formed by the electric discharge and tritium gas.

Labeling techniques using an electrical discharge method were first applied to simple organic molecules (Dorfman and Wilzbach, J. Phys. Chem. 63, 799 (1959)), but these techniques appear to present formidable problems with proteins. Angiotensin II, a small peptide, has been labeled using an electric arc and after purification (40% recovery) exhibited undiminished pressor and oxytoxic activity (Khairallah et al., Arch.

Biochem. Biophys. 171, 729 (1962)). Recently, Noyer et al., J. Label. Compd. Radiopharm. 72, 365 (1976) have reported the labeling of ribonuclease in such a manner. Even though high specific activities (2-10 Ci/mmol) were achieved, extensive decomposition and low enzyme activities (32-68%) were also obtained. Moreover, it is not clear whether the radioactivity is associated with the active enzyme or the inactive decomposition products. Still further, Wolfgang et al., J.A.C.S. 78, 5132 (1956) disclose a method of labeling in which a substance in a tritium atmosphere is subjected to an electric discharge between electrodes of a potential difference of 500 volts.

A range of organic compounds, including amino acids, peptides and proteins, has been tritiated utilizing microwave discharge activation of tritium gas as disclosed by Hembree et al., J. Biol. Chem. 239, 3741 (1973). A free radical mechanism is probably responsible for tritium incorporation in this discharge method. High specific activities (up to 15 Ci/mmol) were obtained for many of the compounds tritiated by the microwave discharge method, but extensive purification of the products obtained was required. For each compound studied, the crude preparation after the removal of easily exchangeable tritium contained impurities of high specific activity which represented from 50 to 90% of the residual tritium.

Three peptides (H-Leu-Tyr-Leu-OH, H-Ile-Ile-D-Val-OH and H-Val-Ala-Ala-Phe-OH) were tritiated by this method as disclosed by Hembree et al., J. Biol. Chem. 248, 5532 (1973) to specific activities of 0.1-2.0 Ci/mmole after purification. The protein hormones adrenocorticotropin (ACTH), luteinizing hormone (LH) and follicle-stimulating hormone (FSH) were also tritiated. The ACTH preparations had specific activities of 0.3-14.5 Ci/mmole. The specific activities of the products were highest when small samples were tritiated and were 1000 times greater than the activities obtained from the technique employed by Wilzbach using similar amounts of ACTH.

It is apparent from the above discussion that the microwave discharge procedure represents a significant advance in the field of tritium labeling of proteins and other biological molecules. The highest incorporation of tritium in a molecule (0.5 tritium atoms per molecule) has been achieved by this procedure. Yet, extensive decomposition of the substrate molecules still occurs during labeling under microwave discharge conditions. This is not unexpected since it is well known that the action of ionizing radiation on proteins causes main chain disruptions, polymerizations, chemical modifications of side chains and results in severe conformational damage. Separation of highly radioactive by-products from the labeled protein limits the usefulness of this procedure.

In the free radical interceptor method the protein is first irradiated with $\gamma$-rays or exposed to an electrical discharge from a Tesla coil. Free radicals are formed and subsequent exposure to tritiated hydrogen sulfide yields a tritiated protein. Exchangeable tritium is then removed by dialysis. Lysozyme and ribonuclease have both been tritiated by this procedure using $\gamma$-irradiation as shown by White and Riecz, Biochem. Biophys. Res. Comm. 30, 303 (1968). In each case, chromatography of the reaction product revealed the presence of impurities formed in the reaction; however, the major peak is reported to have the full enzyme activity. Similar results were obtained with lysozyme, ribonuclease and actin which were tritiated using an electrical discharge as shown by White et al., Anal. Biochem. 30, 245 (1969). Repeated crystallization of the lysozyme resulted in a drop in the specific activity from 40 to 13 Ci/mole. Since the enzyme activity did not change, it was thought that the procedure was simply removing some exchangeable tritium. In contrast, the enzyme activity of labeled lysozyme prepared by the technique of Wilzbach was substantially altered by crystallization.

The problems of the previously discussed tritiation methods are shared by the free radical interceptor method. Free radicals are extremely reactive and can undergo many types of reactions, most of which would degrade the protein. In addition, the method does not appear to be very reproducable.

Still other attempts have been made to incorporate tritium into a variety of protein substrates by several of the techniques discussed above as summarized in Table 1 below.

TABLE 1

Tritium Labeling of Proteins by Gas Exposure Methods

| Compound | Tritiation Method | Sp. Act. $\mu$Ci/mg | mole tritium/ mole substrate | References |
|---|---|---|---|---|
| ACTH | Wilzbach | 1.8 | 0.00025 | Nishizawa et al., Can. J. Biochem. 43, 1489 (1965) |
| Lysozyme ribonuclease | Wilzbach | — | 0.0018 | Steinberg et al., Science 126, 447 (1957). |
| Insulin | Wilzbach | 4.6 | 0.00083 | Von Holt et al., Biochim. biophys. Acta 38, 88 (1960) Von Holt and Von Holt, Naturwissenschaften 45, 289 (1958) |
| Thyrotropin releasing hormone (TRH) (a tripeptide) | Wilzbach | 8000 | 0.1 | Schally and Redding, Int. J. Appl. Radiat. Isotopes 21, 742 (1970) |
| Vasopressin | Electrical discharge | 400 | 0.01 | Fong et al., Proc. Nat. Acad. Sci. 46 1273 (1960) |
| Angiotensin II | Electric arc | 300 | — | Khairallah et al., Science 138, 523 (1962) |
| Ribonuclease | Electrical discharge | — | 0.09-0.3 | M. Noyer et al., J. Labeled Cmpd. Radiopharm. 12, 365 (1976) |
| Adenocorticotropin (ACTH) | Microwave discharge | 3200 | 0.5 | Hambree et al., J. Biol. Chem. 248, 5532 (1973) |
| $\beta_2$-microglobulin | Microwave discharge | 500-5000 | — | Wassels et al., Radiat. Res. 74, 35 (1978) |
| $\beta$-lipoprotein | Tritium exchange with $CH_3CO_2T$ | 0.72 | — | Cosztonyi et al., Nature 208, 381 (1965) |
| Lysozyme | Free radical | 0.7 | 0.00033 | White and Riecz, Biochem. Biophys. |

TABLE 1-continued

Tritium Labeling of Proteins by Gas Exposure Methods

| Compound | Tritiation Method | Sp. Act. μCi/mg | mole tritium/ mole substrate | References |
| --- | --- | --- | --- | --- |
| ribonuclease Lysozyme ribonuclease actin | interruptor (γ,HST) Free Radical interceptor (γ,electrical discharge, HST) | 0.4-0.06 | .003 | Res. Comm. 30, 303 (1968) White et al., Anal. Bioch. 30, 295 (1969) |
| Collagen | Free radical interruptor (electrical discharge, HST) | 0.7 | 0.0074 | Labrosse et al., Anal. Bioch. 70, 218 (1976) |

In view of the disadvantages of the above-described tritiation techniques, a need continues to exist for a method of introducing tritium into organic compounds, especially sensitive biological molecules such as proteins, peptides, lipids, nucleic acids and polysaccharides as well as simple organic compounds which are particularly difficult to isolate or synthesize, which does not result in structural modification, loss of activity and deterioration of the substrate molecules.

SUMMARY OF THE INVENTION

Accordingly, an object of the present invention is to provide a technique of incorporating tritium in molecules which does not result in structural modification or deterioration of the molecules.

Another object of the invention is to provide a method for tritiating sensitive biological molecules and molecules which are difficult to isolate or synthesize.

Yet another object of the present invention is to provide a technique for tritiating molecules at low pressure, thereby using relatively small quantities of tritium.

Briefly, these objects and other objects of the present invention as hereinafter will become more readily apparent can be attained by depositing molecules of a substance to be tritiated on a supporting substrate in a vacuum chamber and then subjecting the substance to low pressures of tritium gas. In another embodiment of the invention, a substance is tritiated by placing the same on a supporting substrate in a vacuum chamber near, but not in the path of an electron beam which traverses the chamber, admitting the tritium gas into the chamber and subjecting the tritium to the electron beam, thereby generating vibrationally excited tritium species which collide and react with the deposited substance thus incorporating tritium atoms into the substance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

In the present invention, two methods are provided for the incorporation of the tritium into substances. Method 1 is experimentally simpler than Method 2. However, Method 2 results in higher incorporation of tritium into the target material. Both methods have been used to incorporate tritium into biologically sensitive materials with little or no deterioration or loss of biological activity.

A variety of substances containing hydrogen can be labeled with tritium by the techniques of the present invention. Because the substance to be tritiated is not directly subjected to a source of high energy, such sensitive biological molecules as proteins, peptides, lipids, and polysaccharides as well as organic molecules which are difficult to synthesize or isolate are particularly amenable to the present techniques. Suitable examples of biologically sensitive molecules include lysozyme, ribonuclease, insulin, oxytoxin, thyrotropin, vasopressin, angiotensin II, ribonuclease, adenocorticotropin (ACTH), $\beta_2$-microglobulin, hemoglobin, $\beta$-lipoprotein, actin, collagen, follicle-stimulating hormone (FSH), luteinizing hormone (LH), gonadotropin, $\alpha$-globulin, tetanus toxin and the like. Suitable examples of organic compounds include desmosine, cholesterol, phosphotidylethanol amine, sucrose and glycine, as well as non biologically sensitive compounds such as synthetic and natural polymers. Other suitable compounds include inorganic compounds such as metal hydrides as well as organometallic compounds and vitamin $B_{12}$. Of course, the present invention is not limited to only such preferred molecular substrates but, in fact, any substance containing hydrogen atoms which can be exchanged with tritium by the present technique can be employed. Other suitable biological organic materials include nucleic acids, nucleotides, polynucleotides of ribonucleic acids or deoxyribonucleic acids, and the like. Hydrogen exchangeable groups include C-H, N-H, O-H, S-H, Si-H and metal-H bonds.

DESCRIPTION OF METHOD 1

This method provides a simple means of tritiation of molecules by exposure of the molecules to small amounts of tritium gas at low pressure. This method is more advantageous than the gas exposure method reported by Wilzbach, J. Am. Chem. Soc. 78, 5132 (1956) and 79, 1013 (1957), because it does not require Curie quantities of tritium gas as are necessary with the Wilzbach method. Additionally, Method 1 of the present invention causes very little degradation of sensitive protein molecules and recovery of enzyme activity after tritiation by this method has been as high as 100%. The tritiation of some proteins at low pressure in the presence of 1000 times less tritium gas than as required by the method of Wilzback has yielded specific radioactivities as high or higher than those obtained with that method but without the attendant degradation of the molecules which occurs when Curie quantities of tritium are used.

In the technique of Method 1, a sample is prepared for labeling by depositing it as a uniform, thin layer on the surface of a stainless steel plate or some other suitable surface such as teflon, glass, a membrane filter or ceramic material. A suitable size for such a plate is 9 by 15 cm, but may be larger or smaller depending upon the amount of material to be labeled. A typical range of material on such a plate is from 0.01 to 10 mg/cm$^2$, but more or less dense deposits could certainly be used. The method of deposition is dependent upon the properties of the material to be tritiated. Proteins and other sensitive organic materials are most conveniently deposited by lyophilization directly onto the plate. If possible, it is best to lyophilize substrates from pure water so that only the material to be tritiated is deposited on the plate. However, when necessary for stabilization or solubilization, proteins may be lyophilized from low ionic strength buffers.

Figure 1:
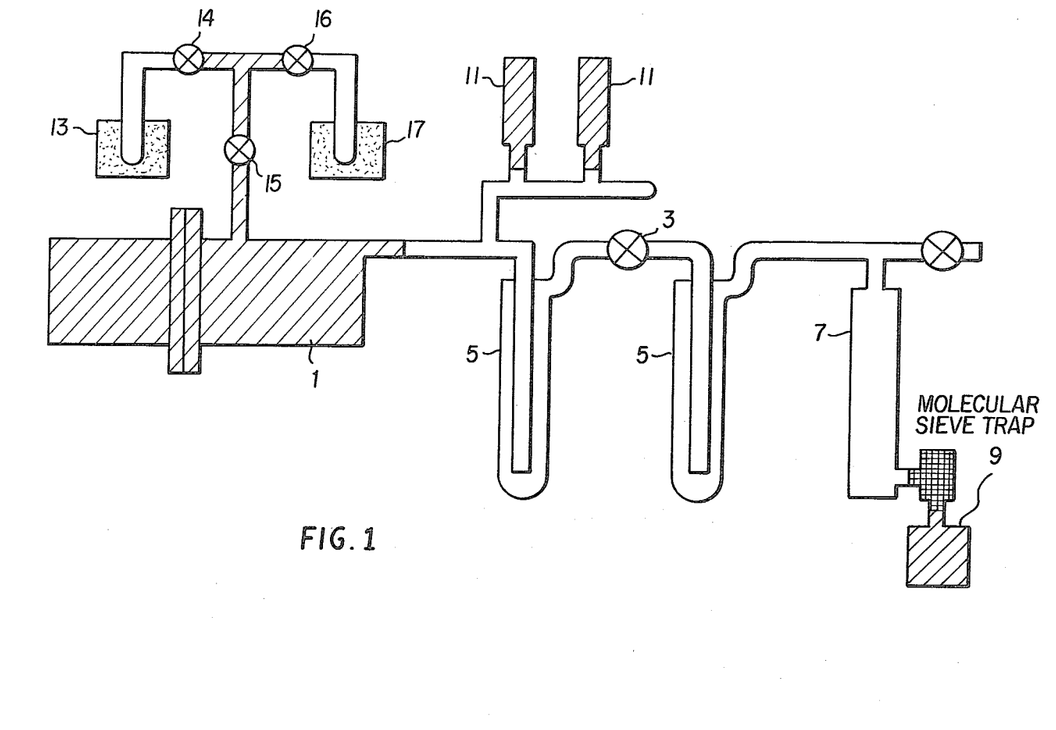
FIG. 1 shows a schematic of the simple low pressure tritiation apparatus used in Method 1 of the present invention.

As shown in FIG. 1, the material deposited on the plate is evacuated inside reaction chamber 1 to a base pressure of at least 0.1 torr to $10^{-8}$ torr preferably $10^{-3}$ to $10^{-8}$ torr. Best results are obtained when the base pressure is in the range of $10^{-7}$ torr. Reaction chamber 1 is closed by valve 3 to isolate the reaction chamber 1 from the pumping system which includes two liquid nitrogen cold traps 5, a diffusion pump 7 and a roughing pump 9. Vacuum gauges 11 provide for measurement of pressures greater than $10^{-3}$ torr (thermocouple gauge) and below $10^{-3}$ to $10^{-8}$ torr (ionization gauge). Tritium gas may be stored in the gaseous state or in a solid state as a tritide of Pd, U, Ti or similar metal in reservoir 13. Gaseous tritium, released from the metal tritide by heating at sufficiently high temperature, is admitted into reaction chamber 1 via valves 14 and 15. The pressure of tritium gas used ranges from $10^{-4}$ to $10^{-1}$ torr, corresponding to approximately 0.5 to 500 milliCuries tritium in the prototype system diagrammed in FIG. 1. The amount of tritium used is dependent upon the total volume of the system and could be reduced by use of a smaller reaction chamber. The temperature at which the tritiation process occurs ranges from 4° K. to the decomposition temperature of the substance being tritiated in both Methods 1 and 2.

The material is allowed to remain in the tritium gas atmosphere for from several minutes to several hundred hours before any remaining tritium gas is adsorbed by Palladium-activated carbon trap 17. Access to the trap is achieved by opening valve 16. After removal of excess tritium gas the reaction chamber is evacuated and maintained at base pressure for a few minutes before the vacuum is broken and the tritiated sample is removed for characterization.

DESCRIPTION OF METHOD 2

Figure 2:
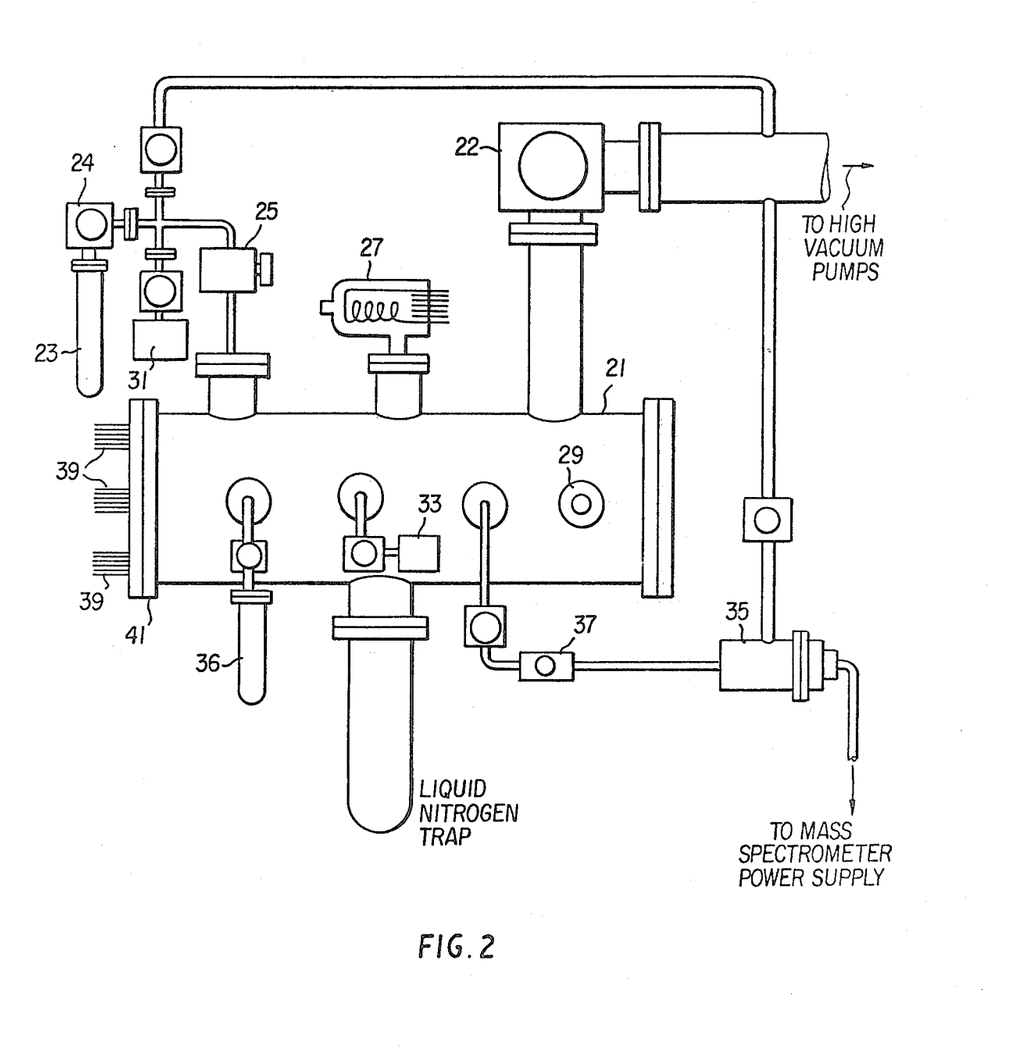
FIG. 2 is a schematic representation of the tritiation apparatus used in Method 2 of the present invention.
Figure 3:
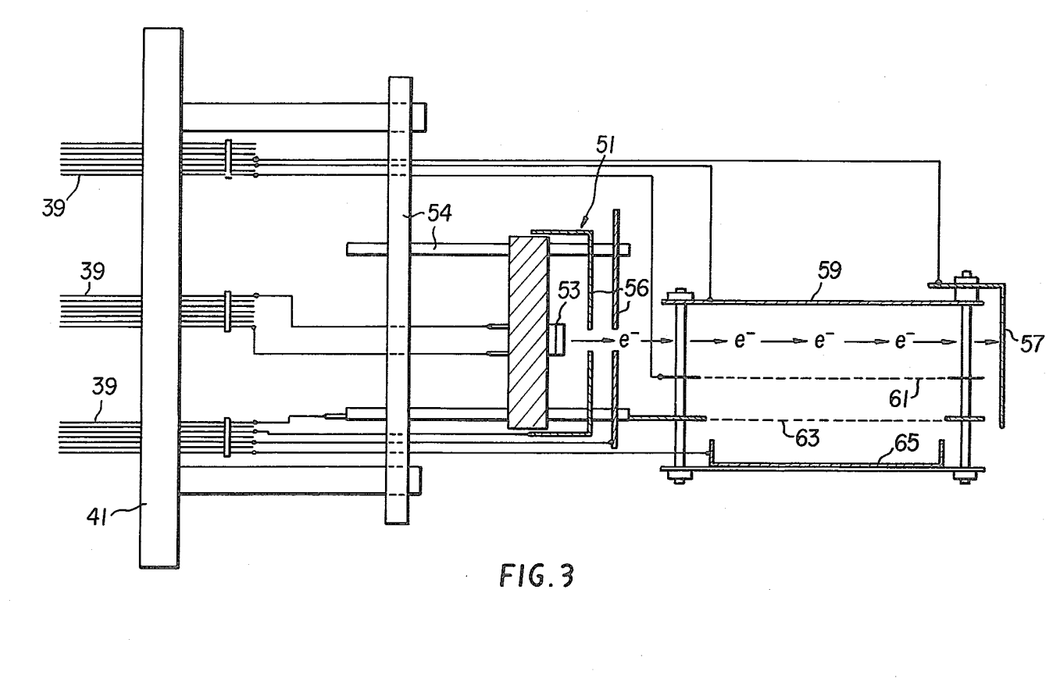
FIG. 3 is a drawing of the tritium ionization source employed in the apparatus of FIG. 2, required by Method 2.

Method 2 is experimentally more complex than Method 1 but the tritium incorporation obtained is higher. The key feature of the method resides in the use of a directionally oriented electron beam which impinges upon gaseous tritium in a reaction chamber, but which does not impinge upon the substance to be tritiated. The electron beam generates vibrationally excited gaseous tritium molecule ions believed to be in the $T_2^+(X^2\Sigma^+g,\nu')$ state by high energy electron impact ionization. The gaseous molecule ions thus generated are accelerated out of the electron impact zone towards the substance to be labeled. Before impact on the deposited substance, the molecule ions can collide with neutral, unexcited tritium molecules of the $(X^1\Sigma^+g,\nu'')$ state thereby generating some fast, vibrationally excited neutral tritium molecules by a charge transfer reaction. The neutral tritium products produced have essentially the same momentum as the fast reactant $T_2^+$ molecule ions produced by electron impact. Accelerated vibrationally excited fast neutral tritium molecules and vibrationally excited tritium molecule ions collide with the solid substance to be tritiated. Exchange of hydrogen for tritium in the substance in the gas-solid interaction is facilitated by the kinetic energy of the impinging fast neutral molecules and molecule ions. This technique results in incorporation of tritium into the solid substance without degradation of the same. FIGS. 2 and 3 provide schematic representations of the apparatus used in Method 2. FIG. 2 is a drawing of the reaction chamber and supporting ancillary equipment. FIG. 3 shows the tritium ionization source that is mounted inside vacuum chamber 21.

Referring to FIG. 2 a vacuum chamber 21 is connected to suitable high vacuum pumping system (not shown) via main valve 22. An example of such a pumping system is the 6 inch diameter oil diffusion pump and the 50 liter per minute mechanical roughing pump used in the prototype tritiation apparatus. Tritium gas is admitted into vacuum chamber 21 from tritium reservoir 23 via valve 24 and fine control needle valve 25. As in Method 1 of the present invention, tritium may be released by heating or by any other convenient method. Appropriate pressure sensing devices including ionization tube 27, thermal conductivity gauge 29, and pressure conductivity manometers 31 and 33 are provided for measurement of the pressure in the system. The vacuum chamber 21 is provided with a trap 36 containing Pd/C which absorbs tritium gas after tritiation of the sample. The composition of gas present in the vacuum chamber at any given time may be determined by sampling an aliquot of the gas into the quadrupole mass spectrometer 35 via sampling valves 37.

Referring to FIGS. 2 and 3, the tritium ionization source 51 is mounted on high vacuum flange 41 which provides the necessary electrical feedthroughs 39 to electron source 53 and ion acceleration assembly 55. Electrons produced by electron source 53 in support structure 54 are accelerated into ion acceleration assembly 55 as a high defined beam that is prevented from impinging on the target substance. This beam of electrons ionizes tritium gas in the ion acceleration region 55 by high energy electron impact ionization initially producing predominately vibrationally excited tritium molecule ions believed to be in the $T_2^+(X^2\Sigma^+g,\nu')$ state. The electron beam is collected by electron trap 57. The electron beam generating system is conventional so that any source of electrons such as metal oxide composite emitters or metal ribbons can be employed. Suitable electron energies range from 5 to 1500 electron volts. An important feature of the design of this system is the collimation of the electron beam by focussing means 56 in such a way that the material to be labeled is never in the path of free electrons and high energy electrons do not impinge on the target substrate.

The kinetic energy of the molecule ion beam striking supported substance and target plate 65 can be varied from 0.01 eV to 2000 eV by appropriate selection of acceleration potentials applied to ion repeller plate 59, ion acceleration screens 61 and 63 and to the target plate 65 itself. Target plate 65 is maintained at a sufficiently negative potential to accelerate the tritium ions to it.

As discussed above, as the vibrationally excited tritium molecule ions traverse the chamber to the substance to be labeled, they can collide with unexcited tritium molecules thereby generating vibrationally excited fast neutral tritium molecules which also are conveyed to the supported substance. Both the neutral and ionic tritium gas molecules collide with the substance to be labeled and exchange with exchangeable hydrogen atoms in the substance. At very low ion energies it is also possible to produce $T_3^+$ ions which can also accelerate toward the substrate and react with it to produce a tritiated product.

Preparation of the sample for tritiation by Method 2 proceeds just as in Method 1. The material is deposited as a uniform, thin film directly on the bottom of a small rectangular stainless steel boat or any other suitable inert material which can then be placed on the bottom of the boat. Two different sizes have been used in the prototype system, the larger having dimensions 2 cm depth by 5 cm width by 8 cm length and the smaller having dimensions 1 cm depth by 3.8 cm width by 5 cm length, although these dimensions are not critical dimensions. The dimensions of the ion acceleration assembly 55 are smaller for the smaller target plate. The dimensions of the ion acceleration assembly are limited only by the physical limitations governing the generation of a uniform, collimated electron beam in the tritium ionization region between repeller plate 59 and acceleration screen 61. An upper limit is reached when it is no longer possible to cause the majority of the electrons to travel all the way to electron trap 57 without being first deflected upwards toward repeller plate 59 and stopped there.

The substance to be tritiated, deposited on the target plate, is mounted in the ion acceleration assemply, placed inside vacuum chamber 21 and the pressure in the entire system is reduced to a level from $10^{-3}$ to $10^{-9}$ torr or below. This can be readily accomplished by conventional vacuum techniques. Once a proper vacuum is achieved, tritium gas is leaked into the chamber via fine control needle valve 25. Base pressures below $10^{-6}$ torr are best. The optimum tritium pressure during the tritiation reaction ranges from $10^{-8}$ to $10^{-2}$ torr. However, pressures up to $10^2$ mm of Hg could be used, but would result in the use of large amounts of tritium. Lower limits are dependent on the residual background pressure of the system. The tritiation process can be conducted for from several minutes to several hundred hours. Under a particular set of experimental conditions, longer times result in greater degrees of tritiation. The tritiation process is usually conducted at ambient temperature. However, sensitive samples may require lower temperatures which may be provided via liquid nitrogen feed-throughs to the sample stage 65. The temperature range utilized is determined by the stability of the sample. There appear to be no limitations on the size of the sample utilized. Tritium may be purchased and admitted in any convenient manner.

The techniques of the present invention provide for the effective labeling of various substances by two effective methods which require 1000-fold less tritium gas than required by the technique described in Wilzbach above. Specific radioactivity levels as high or higher than the activity levels of tritiated substances obtained from the Wilzbach procedure can be achieved. Very little degradation of sensitive biological molecules occurs when the present processes are used on the same and recoveries of enzymatic activity as high as 100% after purification of the labeled product can be achieved.

Having now generally described the invention a further understanding can be obtained by reference to certain specific examples which are provided herein for purposes of illustration only and are not intended to be limiting unless otherwise specified.

EXAMPLES

EXAMPLE 1 METHOD 1

The Zn-containing endopeptidase thermolysin isolated from the bacterium *Bacillus thermoproteolyticus* was tritiated by Method 1. A 26 mg amount of enzyme was lyophilized from a solution of 1.0 mM $Ca(OAc)_2$ onto a 9 cm wide by 15 cm long semicylindrical stainless steel plate. After evacuation in reaction chamber 1 to a base pressure of $1 \times 10^{-6}$ torr, 5 millicuries tritium gas was admitted to a final pressure of $1 \times 10^{-3}$ torr. The reaction was allowed to proceed for 62 hours before excess tritium was removed by trapping on Pd and the system evacuated. The results of this typical experiment are shown in Table 2.

After tritiation, the tritiated thermolysin was removed from the reaction chamber and dissolved in cold buffer (0.10 M Tris.HCl, 10 mM $CaCl_2$, pH 7.2). The protein was dialyzed at 4.25° C. to remove readily exchangeable tritium, then purified by affinity chromatography on a column of HONHCOCH-($CH_2C_6H_5$)CO-L-Ala-Gly-NH($CH_2$)$_3$O-agarose. This affinity resin binds thermolysin tightly and specifically at pH 7.2 (0.10 M Tris.HCl, 0.010 M $CaCl_2$) and releases the enzyme when the pH is abruptly changed to pH 9.0 (0.10 Tris.HCL, 0.10 M $CaCl_2$). Less than 5% of the crude dialyzed product failed to bind to the column and was washed through at pH 7.2. This material, which was enzymatically inactive and was probably denatured thermolysin, had the same specific radioactivity as the active thermolysin which was bound to the column. Elution at pH 9.0 yielded a single peak of constant specific radioactivity with full enzymatic activity. Subsequent chromatography on a Sephadex G-75 (registered trademark of Pharmacia Fine Chemicals, Inc.) column at pH 6.0 and re-chromatography on the affinity column yielded a product with constant specific enzyme activity and an apparently constant specific radioactivity. Furthermore, the purified tritiated thermolysin with a specific radioactivity of 72 Ci/mole was shown to have $k_{cat}/K_M = 21,000$ L/mole's for hydrolysis of the synthetic substrate furylacryloylglycyl-L-leucine amide (Walsh et al., Methods Enzymol. 34, 435 (1974)). This value is in accord, within the limits of experimental error, with the value determined for the same enzyme preparation prior to tritiation which gave $k_{cat}/K_M = 18,000$ L/mole's.

TABLE 2

Tritiated Thermolysin Characterization[a]
After Tritiation by Method No. 1

| Sample | Specific Radio-activity (Ci/mole) | Specific enzyme activity[b] ($\mu$mol/S . mg) |
|---|---|---|
| initial product in buffer | 2500 | 0.38 |

TABLE 2-continued

Tritiated Thermolysin Characterization[a]
After Tritiation by Method No. 1

| Sample | Specific Radio-activity (Ci/mole) | Specific enzyme activity[b] ($\mu$mol/S · mg) |
|---|---|---|
| after dialysis and first affinity chromatography | 190 | 0.47 |
| after dialysis, concentration on Sephadex G-75 column | 64 | 0.45 |
| after dialysis and second affinity chromatography | 72 | 0.45 |
| after denaturation chromatography on Sephadex G-10 | 4 | 0 |
| after 6 N HCl hydrolysis, drying and lyophilization twice | 0.82 | — |

[a]Gas exposure conditions: $1 \times 10^{-3}$ torr $T_2$ (5 mCi), 62 h
[b]Substrate was 2.0 M furylacryloylglycyl-L-leucine amide, 0.10 M Tris . HCl, 0.01 M $CaCl_2$, 2% N,N dimethylformamide, pH 7.2

Chromatography of denatured tritiated thermolysin (72 Ci/mole) on a Sephadex G-10 column in the presence of 8 M urea gave a single protein peak with specific radioactivity of 4 Ci/mole and a peak of HTO corresponding to 94% of the tritium originally bound to the protein. After hydrolysis in 6 N HCl for 20 h, followed by drying and two lyophilization, the residual specific radioactivity was found to be 0.8 Ci/mole. Thus, low pressure tritiation by Method 1 leads to exchange of T for H at N-H and O-H bonds in the interior of the enzyme molecule which are not exposed to solvent until the tertiary structure of the protein is destroyed. Tritium remaining after denaturation or hydrolysis represents tritium bound to carbon. Tritiated water (HTO) exchange experiments with other proteins in solution have shown the presence of hydrogens that are non-exchangeable with HTO (Voordouw and Roche, Biochem. 14, 4667 (1975)). For example, in the case of apo-thermolysin (thermolysin with the active site Zn removed), only 247 of 347 potentially exchangeable hydrogens actually exchange with HTO. The hydrogens at these 100 sites must be present in a number of inaccessible regions in the molecular interior where peptide hydrogens can exchange with solvent only after denaturation of the protein.

Experiments with collagen and antithrombin III have shown these proteins to be effectively tritiated by Method No. 1. A number of experiments with collagen in which the times of exposure were varied resulted in specific radioactivities ranging from 90 to 5600 Ci/mole after extensive dialysis to remove the water exchangeable tritium. Sample data are shown in Table 3. The specific radioactivity was observed to increase with the length of time of exposure to $T_2$. Antithrombin III preparations resulted in an average specific radioactivity of 10 Ci/mole after dialysis. The tritiated antithrombin III retained its full inhibitory activity as demonstrated by the stoichiometric inhibition of trypsin. Tritiated collagen and antithrombin III were shown by polyacrylamide gel electrophoresis in the presence of sodium dodecylsulfate to be free of degradation products.

TABLE 3

Exposure of 5 mg Collagen to 5 mCi $T_2$ at $1 \times 10^{-3}$ Torr as a Function of Time

| Time of Exposure (h) | Crude Specific Radioactivity $\mu$Ci/mg |
|---|---|
| 1 | 1 |
| 3 | 1.9 |
| 6 | 2.4 |
| 12 | 17 |

Successful tritiation of procine pancreatic elastase, bovine ribonuclease and human plasma $\alpha_1$-protease inhibitor ($\alpha_1$-antitrypsin) has also been accomplished using Method No. 1.

In addition to the proteins, a wide range of other compounds and materials has been labled by the low pressure technique. The results of these experiments are presented in Table 4.

TABLE 4

Tritiation of Various Types of Compounds and Materials

| Material | Type of Molecule | Crude Tritium Incorporation |
|---|---|---|
| Phosphotidyl Ethanol amine | Lipid | 26.0 mCi/mole |
| Testosterone Sulfate | Steroid | 10 mCi/mole |
| Sucrose | Polysaccharide | 4 mCi/mole |
| Cholesterol | Organic | 1.6-1.7 mCi/mole |
| Ammonium Sulfate | Inorganic | 2.9-5.5 mCi/mole |
| L-Glycine | $\alpha$-amino acid | 4.7-5.0 mCi/mole |
| Desmonine | amino acid | 1.4 mCi/mole |
| E. Coli Strain B | Whole Cells | $1 \times 10^{-4}$ Ci/$10^8$ cells |
| Chicken Blood DNA | Oligonucleotide | 46 $\mu$Ci/g |
| Filter Paper | Cellulose polymer | 22 $\mu$Ci/g |
| Rubber Hose | Natural polymer | 1.2 $\mu$Ci/g |
| Tygon | Synthetic polymer | 0.8 $\mu$Ci/g |
| Nylon | Synthetic polymer | 0.7 $\mu$Ci/g |
| Rubber | Synthetic polymer | 2.6 $\mu$Ci/g |

EXAMPLE 2, METHOD 2

Thermolysin was labeled by Method 2 and the results of a preliminary experiment are presented in Table 5. 5.4 mg purified enzyme was lyophilized from 10.0 mL 1.0 mM $Ca(CH_3CO_2)_2$ on the inner, bottom surface of a stainless steel rectangular container having dimensions of 2 cm depth by 5 cm width by 8 cm length. The density of the protein on the bottom of the container was approximately 0.14 mg/cm$^2$. The sample was evacuated in vacuum chamber 21 until a base pressure of $1 \times 10^{-6}$ torr was achieved. Main valve 22 was closed and approximately 25 millicuries tritium gas was leaked into the chamber to a final pressure of $1 \times 10^{-3}$ torr. The tritium ionization source was operated for 4 hours during which time the electron beam current was maintained at approximately 75 microamperes.

TABLE 5

Tritiated Thermolysin Characterization After Tritiation by Method No. 2

| Sample | Specific Radioactivity (Ci/mole) | Specific Enzyme Activity[a] ($\mu$mol/s/mg) |
|---|---|---|
| initial product in buffer | 13,400 | 0.55 |
| after dialysis | 1,910 | 0.80 |
| after affinity chromatography | 102 | 0.53 |
| after denaturation chromatography on Sephadex G-10 | 21 | 0.00 |

[a]Substrate was 2.0 mM furylacryloylglycyl-1-leucine amide, 0.10 M Tris . HCl, 0.01 M $CaCl_2$, 2% N,N dimethylformamide, pH 7.2.

The potentials in the ion source assembly were such that the ions produced had an average energy of approximately 75 to 100 eV upon impact on the target plate. The residual tritium gas was removed by adsorption in the Pd-carbon trap 36. After evacuation to base pressure for 15 minutes the sample was removed and characterization was begun.

Characterization of the tritiated enzyme was performed essentially as described previously for the product labeled by Method 1. Comparison of Tables 2 and 5 shows that the enzyme labeled by Method 2 had specific radioactivities at least 5 times higher than the enzyme which was labeled by Method 1. Additionally the time required by Method 2 was only 4 hours whereas Method 1 required 62 hours to produce a product with only one-fifth the final tritium content. Clearly Method 2 provides a more efficient means of tritiation.

Using the apparatus shown in FIG. 2 it is possible to perform experiments employing Methods 1 and 2 simultaneously. Two identical plates are prepared with the same amount of protein on each. One plate is mounted in the ion source assembly and the other is placed in the rear of the vacuum chamber in an area that is free of ions. The advantage of this arrangement is that the contribution by the ion beam process of Method 2 can be quantitatively evaluated and compared with a sample which has been tritiated by simple gas exposure according to Method 1 under identical conditions. This procedure can be used to optimize the parameters of the ion source assembly in order to obtain the maximum enhancement of tritiation above the levels obtained by exposure to low pressures of tritium gas. Parameters which must be adjusted include the geometry of the ion assembly and the relative potentials applied to plates 59 and 65 as well as screens 61 and 63.

Figure 4:
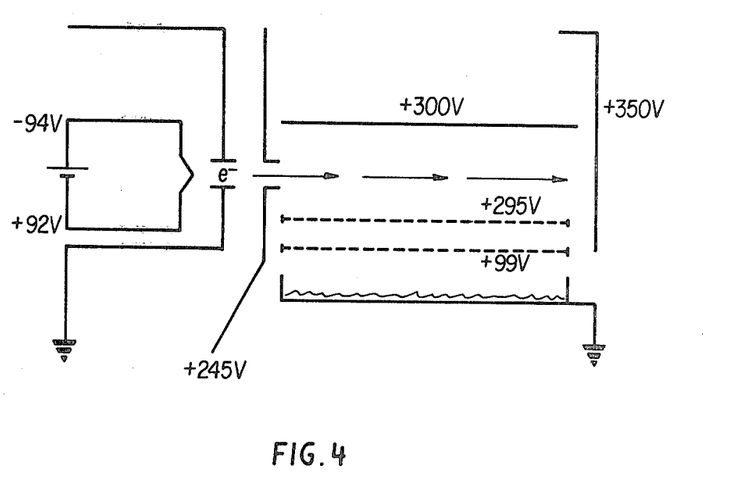
FIG. 4 is an electronic schematic of the ion source assembly of the present invention.

Two 200 mg samples of bovine serum albumin were tritiated simultaneously by both of the present methods. One plate was mounted in the ion source assembly and the control was placed in the rear of the vacuum chamber away from the source of ions. The system was evacuated to a base pressure of $5 \times 10^{-7}$ torr before main valve 22 was closed and approximately 130 millicuries of tritium gas were admitted to a final pressure of $1 \times 10^{-2}$ torr. The electron source was turned on with a filament current of 5.25 amperes. FIG. 4 shows the electronic schematic of the ion source assembly used in this experiment. The quadrupole mass spectrometer was used to monitor the composition of gas present at the beginning of this experiment. The predominant peaks in the mass spectrum at $10^{-5}$ torr were: m/e 3($T^+$), m/e 4($HT^+$), m/e 6($T_2^+$) and m/e 7($HT_2^+$). The experiment was performed for 2 hours before residual tritium was removed and the system evacuated to base pressure.

The sample mounted in the ion source assembly (Method 2) had an average specific radioactivity of 12,600 Ci/mole as compared with the average specific radioactivity of 7,280 Ci/mole for the control sample. An enhancement of tritium incorporation of 72% was observed for the sample subjected to tritium ions. Method 2 was shown to be clearly superior to Method 1. The potential of Method 2 for producing highly tritiated species with little or no decomposition of the same has clearly been demonstrated.

Suitable supporting substrates for the substances to be tritiated by Methods 1 and 2 of the present invention include electrically nonconductive substrates of glass, ceramics, polyfluorocarbon materials, membrane filters and the like. Suitable substrates also include electrically conductive substrates of stainless steel, aluminum and the like. In Method 2, the electron beam is generated using any conventional source of electrons such as metal oxide composite emitters, dispenser cathodes, metal ribbons or wires, or the like.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for tritiating molecules, comprising:
depositing molecules of a substance to be tritiated on a supporting substrate in an evacuated vacuum chamber near, but not in the path of an electron beam which traverses said chamber;
admitting tritium gas into said chamber; and
subjecting said tritium to said electron beam thereby generating vibrationally excited tritium gas molecules and ions which collide and react with the deposited substance thus incorporating tritium atoms in said substance.

2. The method of claim 1, wherein said vibrationally excited tritium gas molecules are a mixture of ionic and neutral excited molecules and atoms of the $T_2^+(X^2\Sigma^+g,v')$, $T_2(X^1\Sigma^+g,v'')$, $T_3^+$, and $T^+$ states respectively.

3. The method of claim 1, wherein said supporting substrate comprises an electrically conductive base which is at a potential which is negative to tritium molecule ions generated by said electron beam.

4. The method of claim 3, wherein said negative potential is a potential of $-300$ volts.

5. The method of claim 1, wherein said electron beam is generated using any conventional source of electrons such as metal oxide composite emitters, dispenser cathodes and suitable metal ribbons or wires.

6. The method of claim 1, wherein said tritium gas is absorbed over Pd on charcoal and is released into said vacuum chamber by heating said Pd on charcoal to 350° C.

7. The method of claim 1, wherein the surface of said supporting substrate having said substance deposited thereon is positioned axially along the direction of said electron beam and perpendicular to the direction of travel of said tritium ions and neutral tritium molecules.

8. The method of claim 1, wherein the energy of said electron beam ranges from 5 to 2000 electron volts.

9. The method of claim 1, wherein the degree of tritiation increases with the time of exposure to the tritium gas.

10. The method of claim 1, wherein the degree of tritiation increases with the time of exposure to the vibrationally excited tritium gas molecules.

11. The method of claim 1, wherein the degree of tritiation increases with the time of exposure to tritium ions $T_2^+$ and $T_3^+$.

12. The method of claim 1, wherein the kinetic energy of said tritium molecule ions impinging on said target substance is variable from 0.01 electron volts to 2000 electron volts.

13. The method of claim 1, wherein said supporting substrate comprises any inert surface such as glass, stainless steel, aluminum, ceramic, teflon, or membrane filters upon which the molecules to be tritiated may be deposited.

14. A method for tritiating molecules, comprising:

depositing molecules of a substance to be tritiated on a supporting substrate in a vacuum chamber;

admitting tritium gas into said chamber to a final tritium gas pressure of less than 0.1 torr; and reacting said deposited substance with the tritium gas admitted into said chamber.

15. The method of claim 1 or 14, wherein said substance is a protein.

16. The method of claim 15, wherein said protein is a fibrous, globular or plasma protein.

17. The method of claim 15, wherein said protein is obtained from mammalian, bacterial or plant sources.

18. The method of claim 1 or 14, wherein said substance is a non-biological organic material.

19. The method of claim 18, wherein said substance is a natural or synthetic polymer.

20. The method of claim 1 or 14, wherein said substance is a sensitive biological molecule selected from the group consisting of proteins, enzymes, glycoproteins, sugars, steroids, amino acids, polypeptides, nucleic acids, lipids, polysaccharides, cells and cellular material.

21. The method of claim 1 or 14, wherein the pressure within the evacuated vacuum chamber is reduced to within the range of $10^{-8}$ to $10^{-3}$ torr.

22. The method of claim 1 or 14, wherein the pressure of tritium gas within the vacuum chamber is within the range of $10^{-4}$ to $10^{-1}$ torr.

23. The method of claim 1 or 14, wherein said substance is a nucleic acid, nucleotide or a polynucleotide of ribonucleic acid or deoxyribonucleic acid.

24. The method of claim 1 or 14, wherein said substance is deposited to a density of 0.01 to 10 mg/cm² on said supporting substrate.

25. The method of claim 1 or 14, wherein said biologically sensitive molecule is deposited on said substrate by lyophilization.

26. The method of claim 1 or 14, wherein said substance is an enzyme.

27. The method of claim 1 or 14, wherein said substance is a glycoprotein.

28. The method of claim 1 or 14, wherein said substance is a lipid.

29. The method of claim 1 or 14, wherein said substance is a carbohydrate.

30. The method of claim 1 or 14, wherein said substance is a steroid.

31. The method of claim 1 or 14, wherein said substance is a nucleotide.

32. The method of claim 1 or 14, wherein said substance is cellular material or cells of plant, bacterial or animal origin.

33. The method of claim 1 or 14, wherein said substance is an inorganic compound containing exchangeable hydrogen.

34. The method of claim 1 or 14, wherein said substance is a mixture of solid materials.

35. The method of claim 1 or 14, wherein hydrogen atom in internal sites of proteins and other biological macromolecules difficult to exchange in water solutions are exchanged with tritium.

36. The method of claim 1 or 14, wherein hydrogen atoms in internal sites of proteins and other biological macromolecules difficult to label in tritiated water solutions are exchanged with tritium.

37. The method of claim 1 or 14, wherein said tritiation is conducted at a temperature from $-4°$ K. to the decomposition temperature of said substance.

38. The method of claim 1 or 14, wherein said substance is tritiated for several minutes to several days.

39. The method of claim 1 or 14, wherein the amount of tritium is dependent upon the volume of the chamber and the temperature of tritiation.

40. The method of claim 1 or 14, wherein said substance is a material containing exchangeable C-H, N-H, O-H, S-H, Si-H or metal-H bonds.

41. The method of claim 1 or 14, wherein the density of said substance controls the extent of tritiation of the same.

42. The methods of claims 1 and 14, wherein small quantities of tritium gas are utilized.

43. The methods of claims 1 and 14, wherein the density of the substance to be tritiated deposited on the supporting substrate is variable and can be used to control the degree of tritium incorporation into the substance.

44. The method of claims 1 and 14, wherein biological molecules can be tritiated with a minimum amount of sample decomposition and loss of biological activity.

45. The method of claim 1 or 14, wherein said substance is a solid organic compound.

46. The method of claim 1 or 14, wherein said substance is an amino acid or peptide.

47. The method of claim 1 or 14, wherein said tritium gas is released into said vacuum chamber by a leak valve from a tritium reservoir.

* * * * *